United States Patent [19]

Youngdale

[11] 4,275,069

[45] * Jun. 23, 1981

[54] ANTI-DIABETIC 1,2-DIHYDRO-2-OXO-6-ALKYL-NICOTINIC ACIDS

[75] Inventor: Gilbert A. Youngdale, Portage, Mich.

[73] Assignee: The Upjohn Company, Kalamazoo, Mich.

[*] Notice: The portion of the term of this patent subsequent to Sep. 2, 1997, has been disclaimed.

[21] Appl. No.: 97,925

[22] Filed: Nov. 28, 1979

Related U.S. Application Data

[63] Continuation-in-part of Ser. No. 5,454, Jan. 22, 1979, Pat. No. 4,220,648.

[51] Int. Cl.$^3$ .................. C07D 213/55; A61K 31/44
[52] U.S. Cl. .................................... 424/266; 546/298; 546/288
[58] Field of Search ........................ 546/298; 424/266

[56] References Cited

PUBLICATIONS

Mariella, Journal of the American Chemical Society, vol. 69, pp. 2670–2672 (1947).

*Primary Examiner*—Alan L. Rotman
*Attorney, Agent, or Firm*—Robert A. Armitage

[57] ABSTRACT

The present invention relates to certain 6-alkyl-1,2-dihydro-2-oxo-nicotinic acid derivatives, their preparation, and antihyperglycemic use.

6 Claims, No Drawings

ANTI-DIABETIC 1,2-DIHYDRO-2-OXO-6-ALKYL-NICOTINIC ACIDS

CROSS REFERENCE TO RELATED APPLICATION

This application is a continuation-in-part of co-pending United States application Ser. No. 005,454, filed Jan. 22, 1979 now U.S. Pat. No. 4,220,648, issued Sept. 2, 1980.

TECHNICAL FIELD

The present invention provides novel organic compounds. In particular, the present invention provides compounds structurally related to pyridine, most especially nicotinic acid. Most particularly, the present invention relates to certain 6-alkyl-1,2-dihydro-2-oxonicotinic acid derivatives.

The present invention further relates to novel methods for the synthesis and use of the novel organic compounds disclosed herein. These novel methods for use relate to the antihyperglycemic effect of administration of the novel organic compounds of the present invention.

Nicotinic acid is structurally related to pyridine, as indicated in formula I, while 1,2-dihydro-2-oxonicotinic acid is structurally identified in formula II.

1,2-Dihydro-2-oxonicotinic acid, like other 2-oxonicotinic acid derivatives, exhibits a tautomeric form, as evidenced by formula III.

This tautomeric form, 2-hydroxynicotinic acid, is present in equilibria with or in place of 1,2-dihydro-2-oxonicotinic acid depending on the environment into which either the formula II or formula III compound is introduced.

Among 1,2-dihydro-2-oxonicotinic acids, there are known numerous 6-alkyl derivatives thereof.

As indicated above, the present invention also relates to antihyperglycemic agents. Hyperglycemia refers to a condition commonly found in patients suffering from mature-onset diabetes mellitus and other diseases in which impairment of pancreatic function is a consequence thereof. Accordingly, hyperglycemic patients are those exhibiting elevated serum glucose levels. Failure to adequately control such elevated serum glucose levels has been associated in such patients with untoward cardiovascular effects (myocardioischemia, stroke, and peripheral vascular diseases), lethargy, coma, and even death.

While conventional treatment for these hyperglycemic conditions may include diet (e.g., restriction of carbohydrate intake) and insulin injection, one important means of treating such patients is with oral antihyperglycemic agents. The most important class of oral antihyperglycemic agents are the sulfonylureas, e.g., tolbutamide, clorpropamide, tolazamide, and glyburide.

As oral antihyperglycemic agents, sulfonylureas have as a primary mechanism of action the induction of endogenous insulin release. Accordingly, these compounds exhibit activity in glucose-primed, fasted, intact rats and glucose-primed, fasted, adrenalectomized rats. However, in other animal preparations, e.g., alloxanized diabetic and eviscerate rats, no antihyperglycemic effect is observed.

Another class of oral antihyperglycemic agents are the biguanidines, principaly phenformin. Unlike the sulfonylureas, the biguanidines do not stimulate endogenous insulin secretion, but are nonetheless effective in lowering elevated blood glucose levels in mature onset diabetics. In non-diabetic subjects, however, no significant antihyperglycemic effect is ordinarily observed upon biguanidine administration.

Yet another class of oral antihyperglycemic agents are represented by certain nicotinic acid derivatives, particularly 1,2-dihydro-2-oxo-nicotinic acid derivatives. Such compounds are, for example, disclosed in German Offenlegungsschrift No. 2,637,477, published Aug. 20, 1976, abstracted at Derwent Farmdoc CPI No. 16112A. The tautomeric form of 1,2-dihydro-2-oxonicotinic acid, 2-hydroxynicotinic acid has been demonstrated to have antihyperglycemic activity in the alloxanized diabetic rat, but this activity has been associated with a decrease of plasma free fatty acids. See Fang, V. F., Arch. int. Pharmacodyn.

PRIOR ART

Orally active antihyperglycemic agents are widely known in the art, as indicated by references cited above.

Particularly, see the references cited above relating to 1,2-dihydro-2-oxonicotinic acids.

Among the 6-alkyl-1,2-dihydro-2-oxonicotinic acids known in the art is 6-isobutyl-1,2-dihydro-2-oxonicotinic acid. This compound is reported by Mariella, R. P., JACS 69:2670 (1947). Other known 1,2-dihydro-6-oxonicotinic acids known include the 6-methyl compound (Dornow, A., Ber. 73:153, 1940), the 6-propyl compound (Gruber, W., et al., Monatsh 81:83, 1950), the isopropyl compound (Kochetkov, N. K., Doklady Akad. Nauk USSR 84:2289, 1952, Chem. Abstract 47:3309, 1953), the 6-cyclopropyl compound (Mariella, R. P., et al., JACS 70:1494, 1948), the 6-n-pentyl compound (Kochetkov, ibid.), and the 6-cyclohexyl compound (U.S. Pat. No. 3,873,523).

SUMMARY OF THE INVENTION

The present invention particularly relates to novel organic compounds.

The present invention further relates to the pharmacological use of such compounds.

The present invention further relates to novel pharmaceutical compositions employing such novel compounds. In particular, the present invention relates to:

A 1,2-dihydro-2-oxonicotinic acid derivative of formula IV, wherein $R_1$ is hydrogen, alkyl of one to 4 carbon atoms, inclusive, or a pharmacologically acceptable cation, and $R_2$ is alkyl of one to four carbon atoms, inclusive.

The present invention further provides:

A method of treating adult-onset diabetes mellitus in a human suffering from said disease which comprises:

orally administering to said human an amount of a 1,2-dihydro-2-oxonicotinic acid derivative of formula IV wherein $R_1$ and $R_2$ are as defined above; effective to reduce or eliminate hyperglycemia.

Finally, there are provided pharmaceutical compositions, particularly:

A oral pharmaceutical composition in unit dosage form comprising an amount of a 1,2-dihydro-2-oxonicotinic acid derivative of formula IV, wherein $R_1$ and $R_2$ are as defined above, sufficient to provide a predetermined antihyperglycemic effect in an adult-onset diabetic human to whom such compositions are periodically administered.

The novel 1,2-dihydro-2-oxo-6-neopentylnicotinic acid and derivatives of the present invention are all antihyperglycemic agents, particularly oral antihyperglycemic agents. This antihyperglycemic activity renders these compounds useful in the treatment of adult-onset diabetes mellitus. Adult-onset diabetes mellitus is a disease characterized by pancreatic dysfunction resulting in insufficient levels of insulin being produced or secreted by the pancreas. This form of diabetes mellitus is distinguished from other pancreatic disorders wherein the capacity of the pancreas to produce insulin is totally abolished. While oral antihyperglycemic agents are uniformly ineffective in treating the latter pancreatic diseases, well-known and well-recognized methods exist in the art for the treatment of adult-onset diabetes mellitus with oral antihyperglycemic agents. The novel 1,2-dihydro-2-oxo-6-(2,2-dimethylalkyl)nicotinic acid derivatives of the present invention are all used in the treatment of adult-onset diabetes mellitus by these well-known and well-recognized methods in the art. Accordingly, a patient to be treated with the novel compounds of the instant invention is first diagnosed as a diabetic by conventional means (e.g., the persistence of elevated serum glucose levels), and a treatment regimen with the 1,2-dihydro-2-oxo-6-(2,2-dimethylalkyl)-nicotinic acid derivatives established so that the elevation in a patient's serum glucose level is either significantly reduced or eliminated. The precise therapeutic endpoint of treatment (i.e., elimination or merely reduction in hyperglycemia) is readily determined by the attending physician based upon the clinical presentation and concomitantly employed treatment. For example, the novel compounds of the instant invention may be employed to significantly reduce hyperglycemia in a patient, with a carbohydrate-restricted diet providing the further measure of control.

While the novel compounds of the instant invention may be administered by any convenient systemic route, these compounds are most significantly and usefully employed as oral antihyperglycemic agents, particularly in solid dosage forms (e.g., capsules and tablets). Alternatively, liquid oral dosage forms (e.g., syrups and elixirs) are alternatively employed. The solid, oral pharmaceutical compositions in accordance with the present invention are all prepared by methods known in the art, e.g., methods for preparing other oral antidiabetic compositions. These pharmaceutical compositions are all prepared by methods well known in the art.

Since an individual patient response to treatment with compounds in accordance with the present invention may vary, effective dosages of the compounds of the instant invention will vary from patient to patient. Ordinarily, an oral dosage of 1 mg/kg of a compound in accordance with the instant invention will be adequate to significantly reduce hyperglycemia in a patient being treated. Repeated dosages (e.g., every 4–12 hr) may be required during the day to maintain the antihyperglycemic effect. Accordingly, dosages in accordance with the present invention may range from as low as about 0.1 mg/kg/dose to as high as about 10 mg/kg/dose, depending upon the patient, frequency of treatment, and observed response. In accordance with well-recognized methods, an attending physician may at first prescribe a relatively small amount of the novel 1,2-dihydro-2-oxo-6-(2,2-dimethylalkyl)-nicotinic acid derivative, with subsequent increases in this dosage as necessary to achieve the desired level of control.

The novel 1,2-dihydro-2-oxo-6-(2,2-dimethylalkyl)-nicotinic acid derivatives of the present invention are prepared in accordance with the methods of Chart A.

The formula XXIII compound of Chart A is prepared from the formula XXI compound via the formula XXII 1,2-dihydro-2-oxo-6-(2,2-dimethylalkyl)-3-cyanopyridine intermediate. The procedure for this reaction sequence is described in Example 1. The formula XXV compound is prepared either directly from the formula XXIII compound or from the formula XXII compound by the formula XXIV compound by esterification. In the compounds of Chart A, $R_2$ is alkyl of one to 4 carbon atoms, inclusive.

The formula XXIII compound is transformed directly into the formula XXV compound by conventional esterification means. Such means include reaction with the appropriate alkylhalide, particularly alkyl iodide, or with the appropriate diazoalkane (e.g., diazomethane).

Alternatively and preferably, the formula XXII compound is transformed to the formula XXIV compound by treatment with an anhydrous hydrogen chloride in the absolute alkanol corresponding to the ester to be prepared. Thereafter, the formula XXIV compound is hydrolyzed (heated in water) to yield the formula XXV product.

The formula XXIII compound is transformed to its corresponding pharmacologically acceptable salt by neutralization with base corresponding to the salt to be prepared.

Salts in accordance with the present invention include pharmacologically acceptable metal cations, amine cations and quaternary ammonium cations. Especially preferred metal cations are those derived from the alkali metals. e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

DESCRIPTION OF THE PREFERRED EMBODIMENTS

Compounds in accordance with the instant invention are all prepared in accordance with the representative examples provided below:

EXAMPLE 1

1,2-Dihydro-6-neopentyl-2-oxonicotinic acid.

A. Sodio derivative of 3-oxo-5,5-dimethylhexanal

A mixture of 142 ml (114 g) of 4,4-dimethyl-2-pentanone and 82 ml (74 g) of ethyl formate is added dropwise during 1.5 hr to a stirred mixture of 1 liter of dry toluene, 3 ml (2.3 g) of absolute ethanol, and 48 g of a 50% dispersion in mineral oil of sodium hydride (24 g of NaH). During the dropwise addition, the reaction mixture is cooled to about 30° C. During the course of the dropwise addition, hydrogen gas evolves and a solid separates. After addition is complete, 500 ml of toluene is added and the resulting mixture stirred for 24 hr. Thereafter the solid is corrected by filtration, washing with toluene, and drying under reduced pressure at 56° C. for 19 hr. There is obtained 148.4 g of the sodio derivative of 3-oxo-5,5-dimethylhexanal as an ivory-colored solid. NMR absorptions are observed at 0.98, 2.3, 4.61, 5.21, and 8.8–9.06$\delta$.

B. 1,2-Dihydro-2-oxo-6-neopentyl-3-cyanopyridine

A mixture of 32.6 g of cyanoacetamide, 63.8 g of the reaction product of part A and 600 ml of dioxane are stirred and heated to reflux for 20 hr. After a solid separates, the mixture is cooled and the solid collected by filtration. After washing with dioxane, the resulting solid is dissolved in a liter of water and acidified with 24 ml of acetic acid. A second solid separates and the resulting mixture is extracted with ethyl acetate (1.5 l) and the combined extracts washed with water (200 ml) and brine (100 ml) and dried over magnesium sulfate. Evaporation of solvent yields 25.6 g of a yellow brown solid (product A).

From the combined filtrate and washings above, dioxane is evaporated yielding a viscous (red-brown) oil. This oil is then slurried with 1 liter of water and acidified with 24 ml of acetic acid. A brown viscous oil separates, and the mixture extracted with ethyl acetate (1.5 l). The combined extracts are then washed with water (200 ml) and brine (100 ml) and dried over magnesium sulfate. Evaporation of the solvent yields 43 g of a dark red viscous oil which is chromatographed on 1.3 kg column of silica gel. Eluting with 10% acetone in dichloromethane (200 ml fractions), 4.28 g of crystalline material is obtained in fractions 21–38 after crystallization from acetone-Skelly-solve B. Melting point is 207°–208° C. Concentration of the filtrate yields a further solid (0.78 g), melting point 207°–208.5° C. Total column yield is 5.06 g (product B).

Product A obtained above is chromatographed on 1.3 kg of silica gel, eluting with 10% acetone in dichloromethane (200 ml fractions). Fractions 19–57 are combined and crystallized from acetone and hexane yielding 15.25 g of crystalline material (white needles), melting point 209°–210° C. Concentration of the filtrate yields 3.6 g of ivory solid (melting point 207°–208.5° C. Evaporation of the solvent from the filtrate yields a solid which is crystallized from acetone in Skellysolve B, yielding 0.59 g of an ivory solid (Melting point 207°–208.5° C.). The crystalline material from fractions 19–57 (15.25 g), and the two solids obtained from the filtrate (3.6 g and 0.59 g) are combined to yield 19.44 g of product (Product C).

Combining products B and C yields 24.5 g of pure 1,2-dihydro-2-oxo-6-neopentyl-3-cyanopyridine. Carbon:hydrogen:nitrogen analyses are 69.5.:7.61:14.42. The mass spectrum exhibits peaks at 190 (molecular), 175, 135, 134, 116, 64, 57, 41, 39, and 29. NMR absorptions are observed at 1.01, 2.59, 6.19, 7.82, and 13.4–13.6$\delta$. Infrared absorptions are observed at 3140, 3120, 3080, 2950, 2220, 1650, 1605, 1565, and 1490 cm$^{-1}$.

C. 1,2-Dihydro-2-oxo-6-neopentyl-3-cyanopyridine (optional procedure)

A mixture of 0.84 g of cyanoacetamide, 1.64 g of the reaction product of part A, and 15 ml of pyridine is stirred and refluxed for 18 hr. During refluxing, a solid separates. After the mixture is cooled and treated with 50 ml of water, the resulting mixture is then placed in an ice bath and acidified with concentrated sulfuric acid. A second solid separates and this second solid is then collected by filtration. The filtered solid is then washed with water and dried, yielding 1.06 g of a brown solid. The filtrate is then extracted with ethyl acetate (100 ml) and the combined extracts washed with water (20 ml), dried over magnesium sulfate, and evaporated to a green oil (0.31 g). The green oil (0.31 g) and brown solid (1.06 g) are combined are chromatographed on 50 g of silica gel, eluted with 10% acetone in dichloromethane (40 ml fractions). Fractions 4–11 were combined and crystallized from acetone and Skellysolve B, yielding 0.76 g of crystals (ivory needles), melting point 209°–210° C. Concentration of the filtrate yields 0.14 g of crystals (buff needles), melting point 207°–208° C. Total product yield is 0.90 g of 1,2-dihydro-2-oxo-6-neopentyl-3-cyanopyridine (47.3%), as compared to the 33.1 percent yield for the reaction in part B.

D. 1,2-Dihydro-2-oxo-6-neopentylnicotinic acid

A mixture of 12.3 g of the reaction product of part B or C and 30 g of sodium hydroxide in 150 ml of water is refluxed for 42 hr. After some (accidental) material loss, the remaining mixture is then diluted with 600 ml of water and filtered. The filtrate is then cooled in an ice bath and acidified with hydrochloric acid. A solid separates and is collected by filtration, washed well with water, and dried, yielding a white solid (11.4 g). Silica gel TLC (thin layer chromatographic) analysis indicates the presence of unreacted starting material. Accordingly the white solid is reacted with 30 g of sodium hydroxide in 200 ml of water and refluxed for an additional 22 hrs. The resulting solution is then diluted with 400 ml of water, cooled in an ice bath, and acidified with concentrated hydrochloric acid. The solid separates, is collected by filtration, is washed well with water, and is dried. The solid is then dissolved in boiling acetone and the solution filtered. Water is then added to the filtrate and 9.7 g of crystals (white needles of pure title product) are obtained upon cooling. Melting point is 193°–195° C. The carbon:hydrogen:nitrogen analyses are 63.23:7.56:6.56. The mass spectrum exhibits peaks at 209 (molecular ion), 194, 165, 153, 136, 135, 57, 41, 39, 29. NMR absorptions (deuterated dimethylsulfoxide solvent) are observed at 0.92, 2.58, 3.2–3.4, 6.52, 8.32, and 13.8–14.0$\delta$. Infrared absorptions are observed at 3280, 3100, 3060, 2680, 1750, 1635, 1615, 1555, 1490, 1340, and 1115 cm$^{-1}$.

EXAMPLE 2

Methyl 1,2-dihydro-2-oxo-6-neopentylnicotinate

A. Dry methanol (250 ml) is saturated with anhydrous hydrochloric acid and the resulting mixture reacted with 11.2 g of the title compound of Example 1. The resulting mixture is then stirred and refluxed for 42 hr. The resulting mixture is then filtered and the filter cake washed with dichloromethane. Evaporation of the solvent from the filtrate and washing yields a solid which is shaken with 150 ml of dichloromethane and 100 ml of water. The aqueous layer is then extracted with dichloromethane (150 ml). The combined dichloromethane-containing solutions are then dried over magnesium sulfate and concentrated to a solid (9.5 g). Chromatography on silica gel, eluting with 75% acetone in dichloromethane (200 ml fractions). Fractions 7–22 are combined yielding 8.4 g of a solid. This solid is then rechromatographed on 600 g of silica gel, eluting with 2% methanol in dichloromethane (200 ml fractions). Fractions 21–42 are combined, yielding 6.7 g of a solid, which is then dissolved in 150 ml of dry methanol. The methanolic solution is then saturated with anhydrous hydrochloric acid and refluxed for 61 hr. After evaporation of solvent, the resulting solid in 200 ml of ethyl acetate are heated to reflux and insoluble material is removed by filtration. The filtrate is then washed with 5% aqueous sodium bicarbonate (200 ml) and water (100 ml). After drying over magnesium sulfate and concentration under reduced pressure, there is obtained pure title product.

To a solution of 2 g of the title product of Example 1 in 200 ml of dry tetrahydrofuran is added an equivalent of ethereal diazomethane. The resulting solution is then allowed to stand for 10 min, whereupon acetic acid is added dropwise. Evaporation of solvent yields crude product which is chromatographed on silica gel, eluting with 40% ethyl acetate in Skellysolve B. Fractions containing pure title product are combined.

EXAMPLE 3

Ethyl 1,2-dihydro-2-oxo-6-neopentyl nicotinate

A. A solution of 1,2-dihydro-2-oxo-6-neopentyl-3-cyanopyridine (8.8 g) and 400 ml of absolute ethanol is cooled in an ice bath and a slow stream of anhydrous hydrogen chloride is passed therethrough for 2 hr. The resulting solution is allowed to stand at ambient temperature for 3 days. Thereafter the solvent is evaporated under reduced pressure at ambient temperature, and the resulting material dissolved in warm trichloromethane. Acetone is added and following cooling the material is recovered by filtration and washed with acetone, yielding ethyl-1,2-dihydro-6-neopentyl-3-pyridinecarboximidate hydrochloride.

B. The reaction product of part A (3 g) is dissolved in 100 ml of water and the solution allowed to stand for 11 days. Thereupon, the pure title product is obtained by filtration, washing with water, and drying to a residue.

EXAMPLE 4

1,2-Dihydro-2-oxo-6-(2,2-dimethylbutyl)-3-pyridinecarboxylic Acid

A. 4,4-Dimethyl-2-hexanone

Cuprous iodide (19.0 gms., 0.098 moles) is placed in 100 ml. of ether and the reaction cooled to −37° C. (dry ice-acetonitrile). Ethyl magnesium bromide (3.0 mole solution, in ether, 70 ml., 210 mmoles) is then added slowly. The addition takes place over a twenty-minute period, and during this time the temperature of the reaction is never allowed to exceed −30° C. The blackish solution is allowed to cool at −37° C. and mesityl oxide (10 gms., 0.102 mole) (in ether, 50 ml.) is added dropwise. Mesityl oxide is added at such a rate so as to keep the temperature of reaction less than or equal to −10° C. Fifteen minutes after the completion of the reaction the suspension is poured onto 250 ml. of a saturated ammonium chloride solution. The organic layer is separated from the aqueous layer extracted with (3×50 ml.) portions of ether. The ether layers are combined and dried over magnesium sulfate. The drying agent is removed by vacuum filtration and the solvent removed under reduced pressure to yield a yellow oil. The oil is distilled under reduced pressure and gives two fractions: Fraction two contains 5.3 gms. (42%) of the titled compound as a yellow oil. The carbon:hydrogen analyses are 73.19 to 12.10. The mass spectrum exhibits peak at 73 (molecular ion), 71, 70, 59, 58, 57, 55, 43, 41, and 29. NMR absorptions are observed at 0.85 to 1.05, 1.25, 2.15, and 2.35$\delta$. Infrared absorptions are observed at 1715, 1465, 1360, 1150, cm$^{-1}$.

B. A Sodium salt of 3-oxo-5,5-dimethylheptylaldehyde

A mixture of the total compound of Part A (12.34 gms., 0.096 mole) and ethyl formate (7.11 gms., 0.096 mole) are added dropwise to a suspension of sodium hydride (3.98 gms., 0.096 mole, 59.2% oil dispersion) in toluene (200 ml.). After addition of approximately eight ml. of the reagents, the reaction refuses to proceed. Addition is stopped at this point and the temperature of the reaction is raised to 40° C. Hydrogen evolution begins after ten minutes. This is noted by the use of a bubbler. Heating is discontinued. Addition is restarted and lasts for two and one-half hours. After this time solids form and stop the stirrer. Suspension is allowed to stand overnight at room temperature—eighteen hours. The resultant titled compound is filtered and dried overnight under vacuum. This titled compound weighs 13.9 gms. (89.6%). It is used without further purification.

C. 1,2-Dihydro-2-oxo-6-(2,2-dimethylbutyl)-3-pyridinecarbonitrile

The titled compound of Part B (13.9 gms., 0.085 mole) is suspended in pyridine and cyanoacetamide (7.46 gms., 0.085 mole) is added. The resultant suspension is heated to 120° C. (reflux) and stirred magnetically. The suspension becomes reddish within one hour. This suspension is allowed to reflux for eighteen additional hours. Following this, the suspension is cooled to room temperature and is diluted with 300 ml. of water. At this point all solids dissolve and yield a brown, black solution. Acidification is done with concentrated sulfuric acid, and the black solid which deposits is filtered by vacuum and dried overnight in a vacuum oven. The resulting 15.5 gms. of solid is placed on one kilogram of silica gel and eluted from the column with 5% acetone methylene chloride. The various fractions are combined on the basis of TLC (2.54 cm by 10.16 cm silica gel plates using 10% acetone methylene chloride as the developing agent). The titled compound is isolated in fractions 30–62 and yields 6.2 gms. of an off-white solid. This material is recrystallized from ether methylene chloride hexane to give 5.2 gms. (29.9% of the titled compound as an off-white solid with a melting point of 163°–165° C. Carbon:hydrogen:nitrogen analyses are 70.32 to 7.95 to 13.49. The Mass Spectrum exhibits peak at 209 (molecular ion), 189, 175, 135, 134, 71, 55, 43, 41 and 29. NMR absorptions are observed at 0.8 to 1.1, 1.35, 6.2 and 7.8δ. Infrared absorptions are observed at 3310, 3150, 2780, 2730, 2220, 1670, 1640, 1610, 1555, and 1495 cm$^{-1}$.

D. 1,2-Dihydro-2-oxo-6-(2,2-dimethylbutyl)-3-pyridinecarboxylic Acid

The titled compound of Part 3, (5.3 gms., 0.026 mole) is suspended in 20 ml. of 90% sulfuric acid-water and heated to 120° C. for sixty-six hours. After this time the black acid solution is diluted with water, 100 ml., and a precipitate develops. This precipitate is filtered and then dissolved in chloroform. The chloroform is then treated with activated charcoal and magnesium sulfate. The drying agents and the charcoal are filtered. The resultant solution is then diluted with ether. An off-white solid forms and is filtered. A second crop of solids is subsequently filtered, (0.70 gms.). The two crops of solids are combined on the basis of TLC data (2.54 cm by 10.16 cm silica plates with 20% methanol-methylene chloride as developing agent). The combination of the two crops gives 3.9 gms. of the titled compound, 67% as an off-white solid, melting point of 170°-172° C. The carbon:hydrogen:nitrogen analyses are 64.61 to 7.79 to 6.27. The mass spectrum exhibits peak at 223 (molecular ion), 174, 153, 136, 135, 71, 55, 43, 41 and 39. NMR absorptions are observed at 0.8 to 1.2, 1.4, 2.7, 6.6, 8.65 and 12.3δ. Infrared absorptions are observed at 3260, 3040, 2800, 1745, 1710, 1645, 1610, and 1550 cm$^{-1}$.

FORMULAS

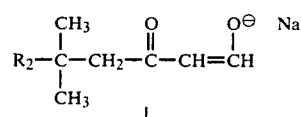

-continued
CHART A

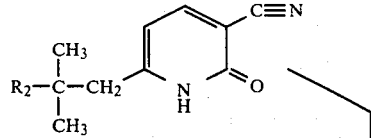  XXII

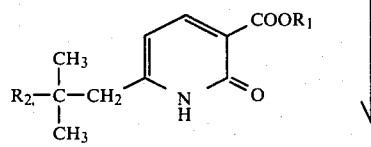  XXIII

  XXIV

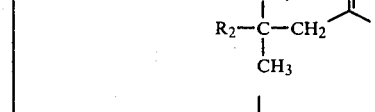  XXV

What is claimed is:

1. A 1,2-dihydro-2-oxo-nicotinic acid derivative of the formula

where $R_1$ is hydrogen or alkyl of one to four carbon atoms, inclusive, and $R_2$ is alkyl of two to four carbon atoms, inclusive, or the pharmacologically acceptable salts thereof.

2. 1,2-Dihydro-2-oxo-6-(2,2-dimethylbutyl)nicotinic acid, a compound according to claim 1.

3. A method of treating a human suffering from adult-onset diabetes mellitus which comprises orally administering to said human an amount of exert a predetermined systemic antihyperglycemic effect of a 1,2-dihydro-2-oxo-nicotinic acid of the formula

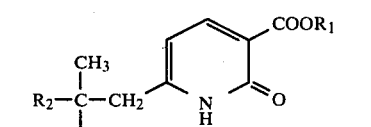

wherein $R_1$ and $R_2$ are as defined in claim 1.

4. A method according to claim 3 wherein said 1,2-dihydro-2-oxo-nicotinic acid is 1,2-dihydro-2-oxo-6-(2,2-dimethylbutyl)nicotinic acid.

5. An oral pharmaceutical composition in unit dosage form comprising an amount to provide an antihyperglycemic effect in an adult-onset diabetic human to whom said composition is administered a 1,2-dihydro-2-oxo-nicotinic acid of the formula

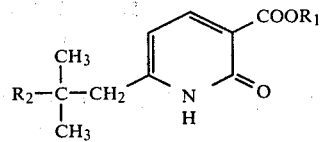

and a suitable pharmaceutical carrier wherein $R_1$ and $R_2$ are defined in claim 1.

6. An oral pharmaceutical composition according to claim 5 wherein said 1,2-dihydro-2-oxo-nicotinic acid derivative is 1,2-dihydro-2-oxo-6(2,2-dimethylbutyl)-nicotinic acid.

* * * * *